United States Patent [19]

Murphy-Chutorian et al.

[11] Patent Number: 5,713,894
[45] Date of Patent: Feb. 3, 1998

[54] COMBINED MECHANICAL/OPTICAL SYSTEM FOR TRANSMYOCARDIAL REVASCULARIZATION

[76] Inventors: Douglas Murphy-Chutorian, 151 Lowell Ave., Palo Alto, Calif. 94301; Stuart D. Harman, 4321 Beechmont Ave., San Jose, Calif. 95136

[21] Appl. No.: 607,782

[22] Filed: Feb. 27, 1996

[51] Int. Cl.$^6$ ................................. A61N 5/06
[52] U.S. Cl. .................. 606/15; 606/7; 606/10; 606/17
[58] Field of Search ................ 433/29, 215; 606/2, 606/6, 7, 10–17

[56] References Cited

U.S. PATENT DOCUMENTS 4,846,171  7/1989  Kauphusman .................. 606/16
5,503,559  4/1996  Vari ............................... 433/29

FOREIGN PATENT DOCUMENTS 0515867  2/1992  European Pat. Off. .
WO 94/14383  7/1994  WIPO .

*Primary Examiner*—David M. Shay
*Attorney, Agent, or Firm*—Janet Kaiser Castaneda

[57] ABSTRACT

The method for combined mechanical/laser myocardial revascularization of a human heart includes: inserting a mechanical piercing device and an elongated flexible lasing apparatus into the chest cavity of a patient; mechanically piercing, micro-tearing or spreading the epicardium of the heart; and then lasing from beneath the epicardium through the myocardium. The apparatus is guided to an area exterior to a ventricle of the patient's heart, and the distal end of the optical fiber apparatus is placed internal to the exterior wall of the heart through an opening which has been created by mechanically piercing, micro-tearing or spreading the epicardium, so that the myocardium and not the epicardium is irradiated with laser energy to allow passage of said optical fiber distal end or said laser energy into the left ventricular cavity without causing a laser irradiation of the epicardium which might be a cause of operative bleeding and for better allowing the sealing of the epicardium after the apparatus is removed.

16 Claims, 8 Drawing Sheets

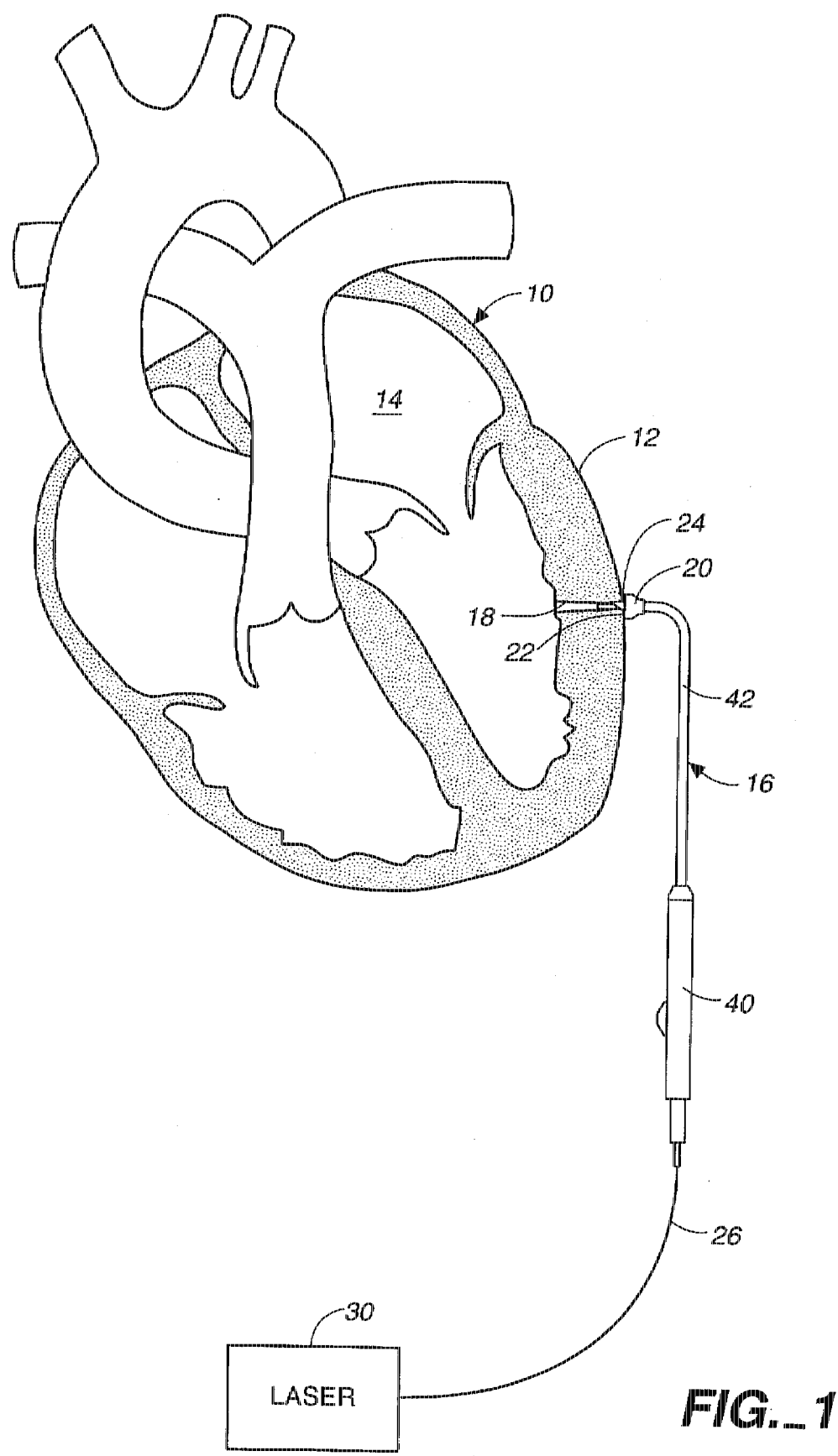
FIG._1

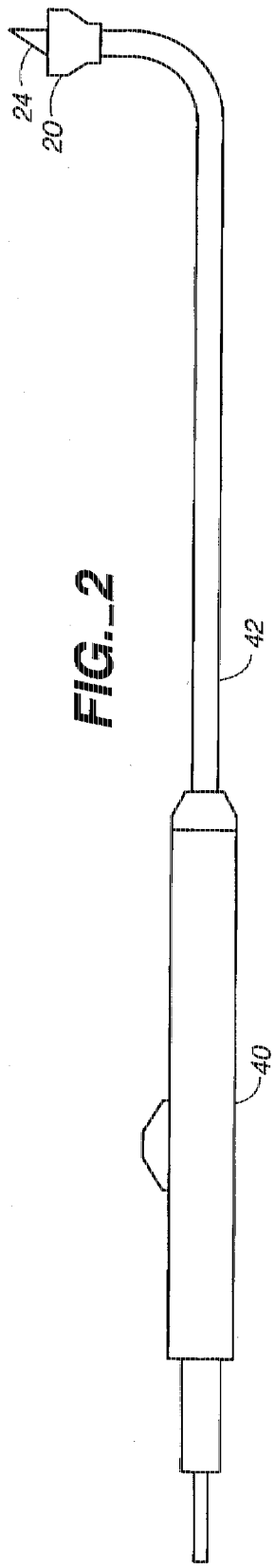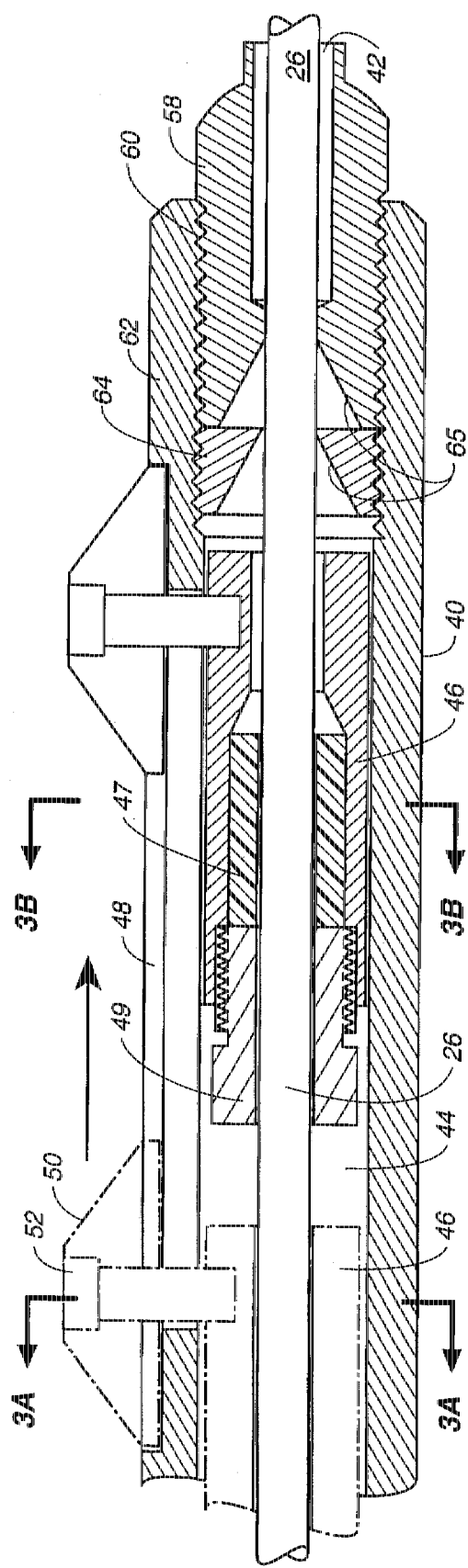

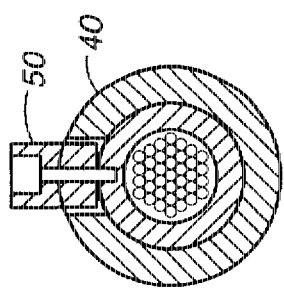
FIG._3A
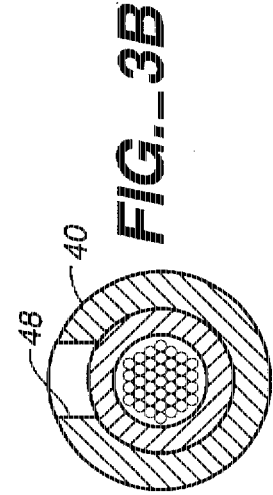
FIG._3B
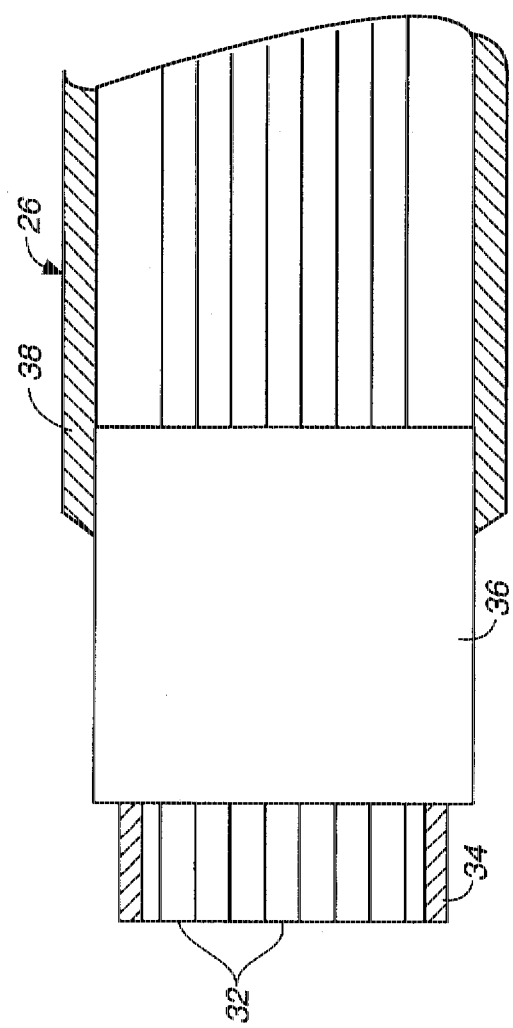
FIG._5A
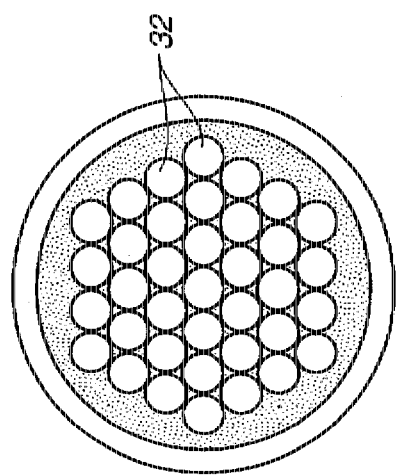
FIG._5

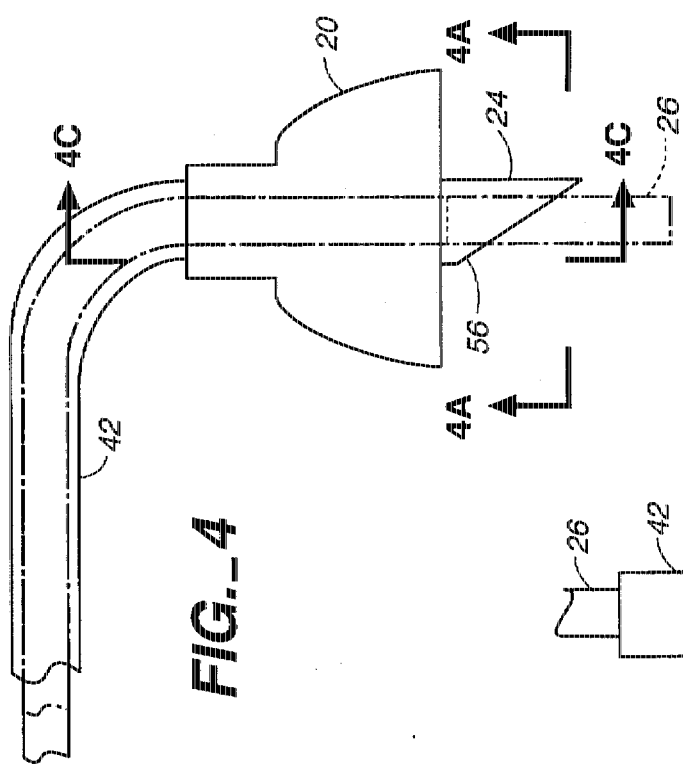
FIG._4
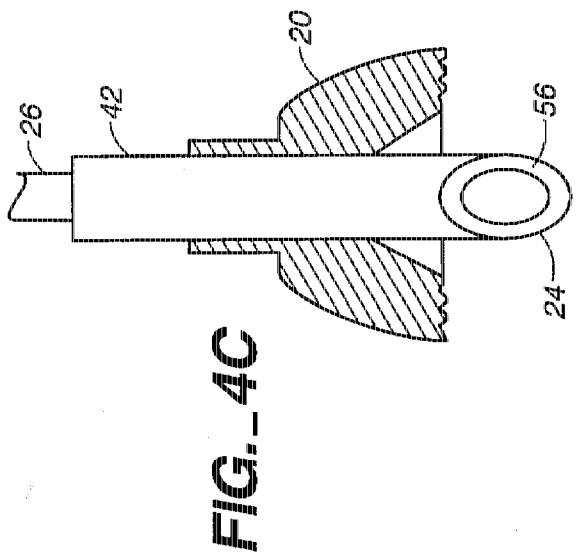
FIG._4C
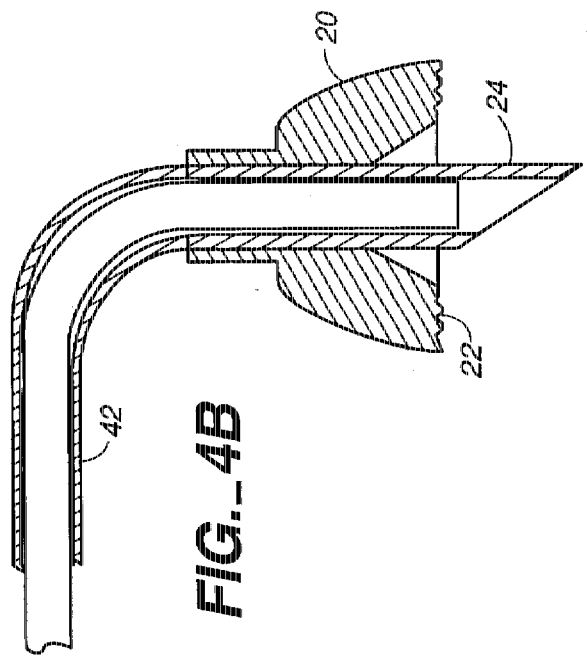
FIG._4B
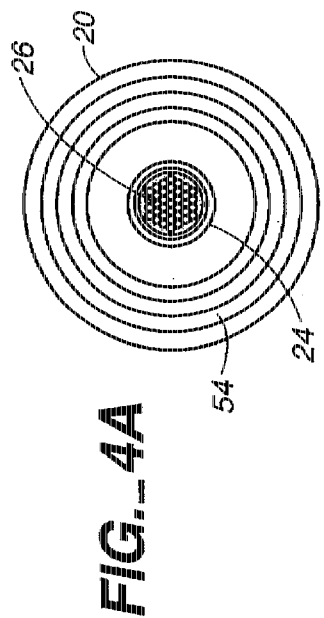
FIG._4A

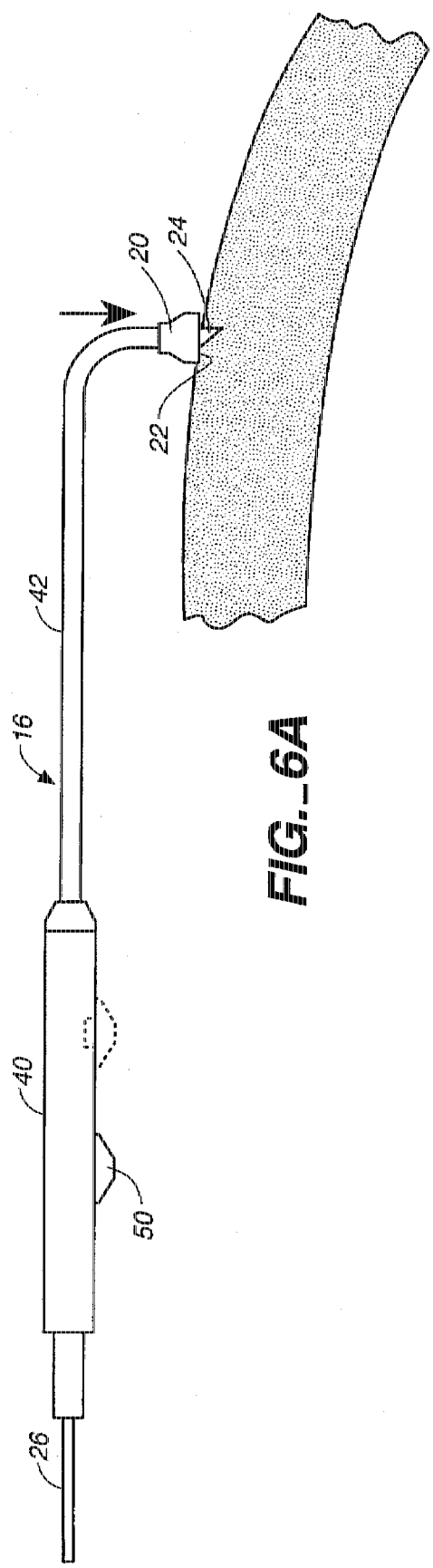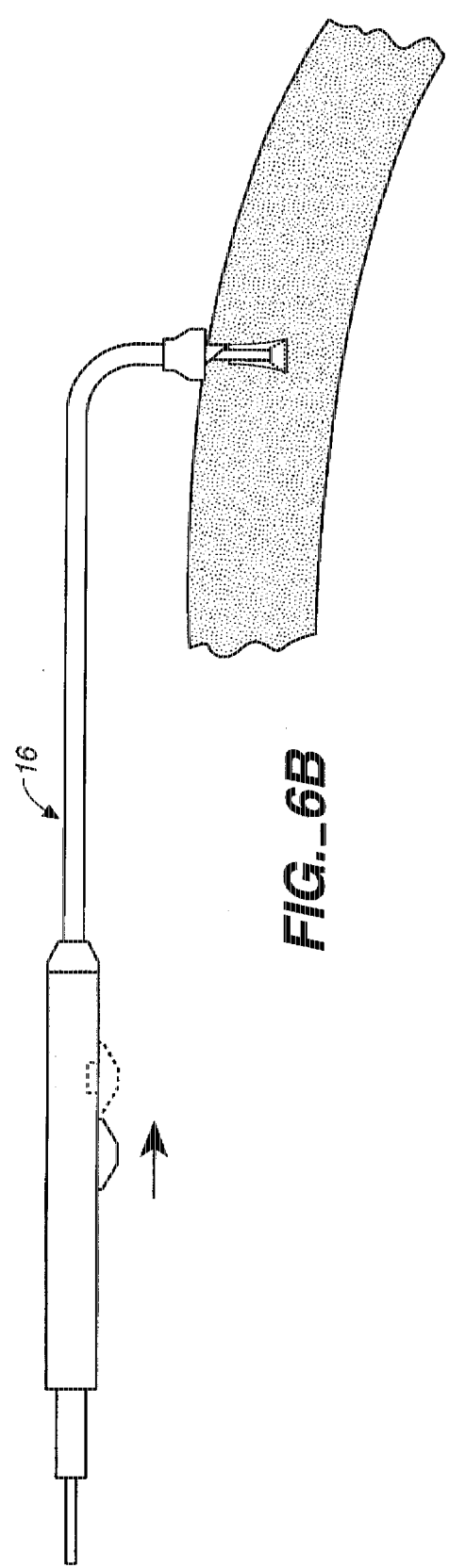

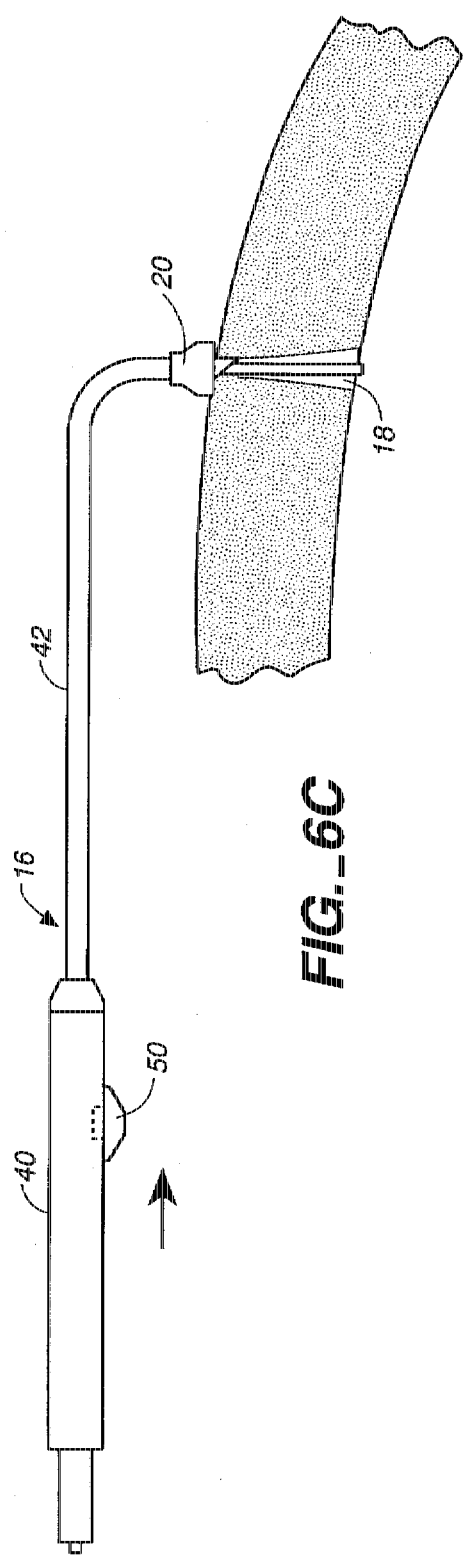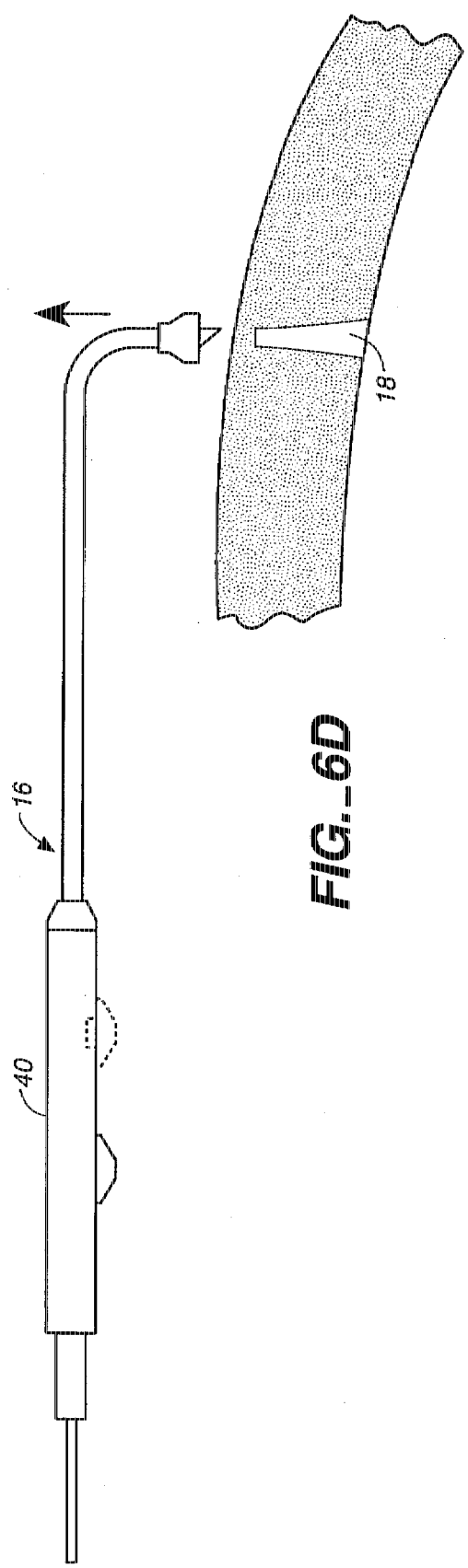

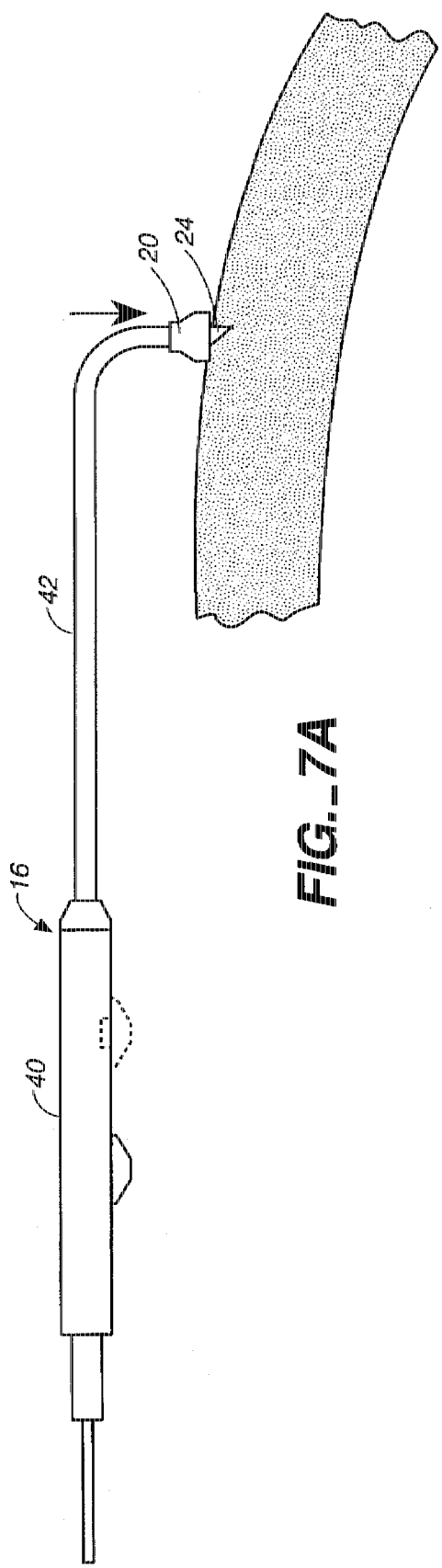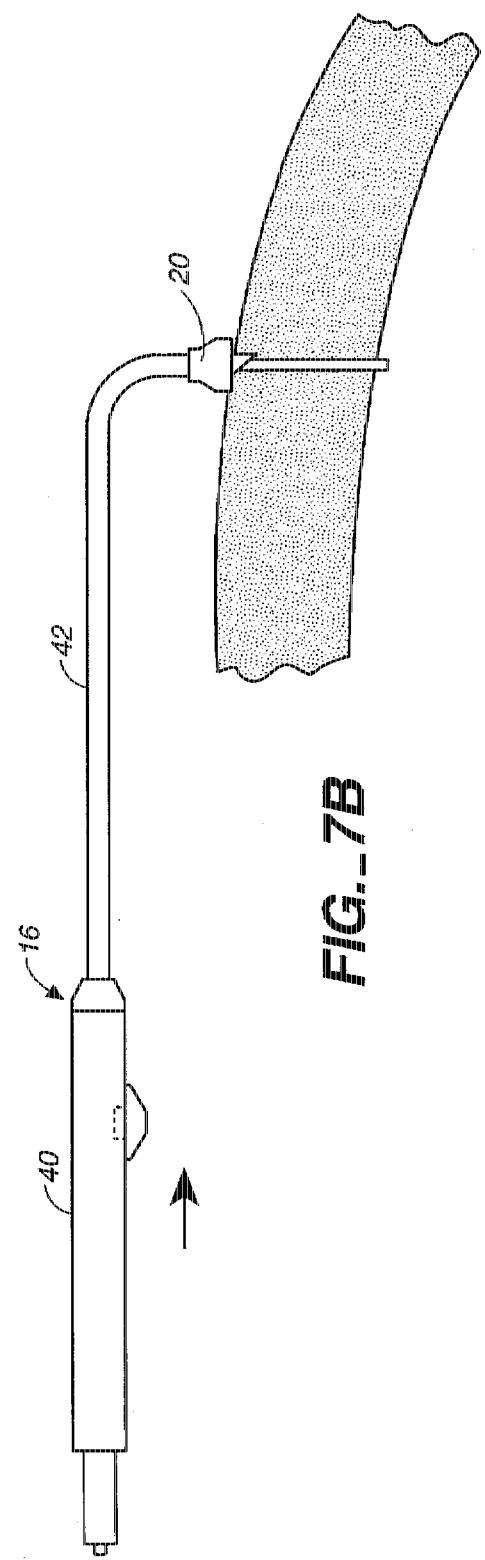

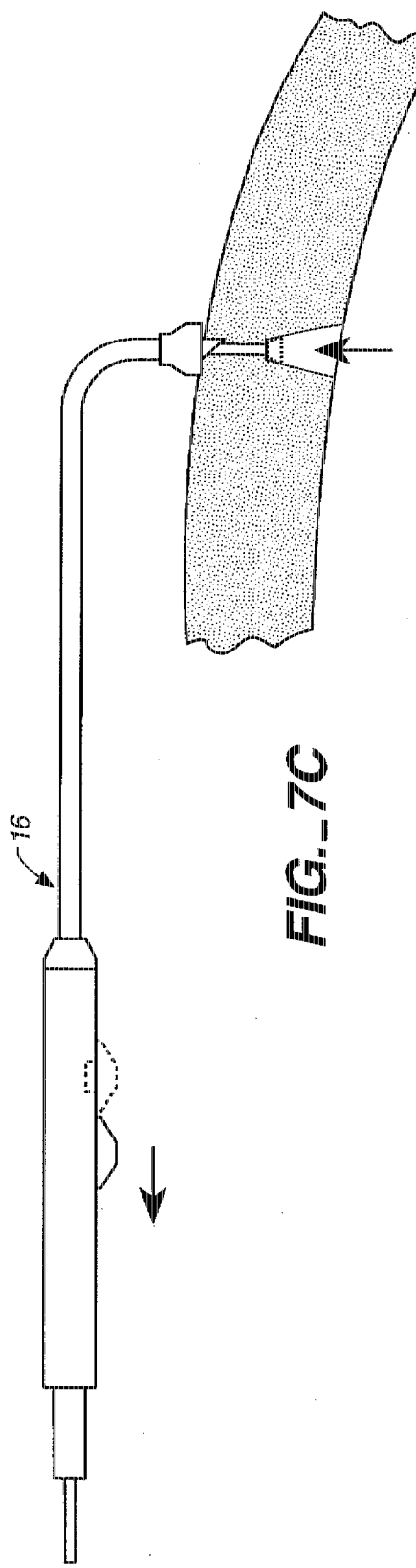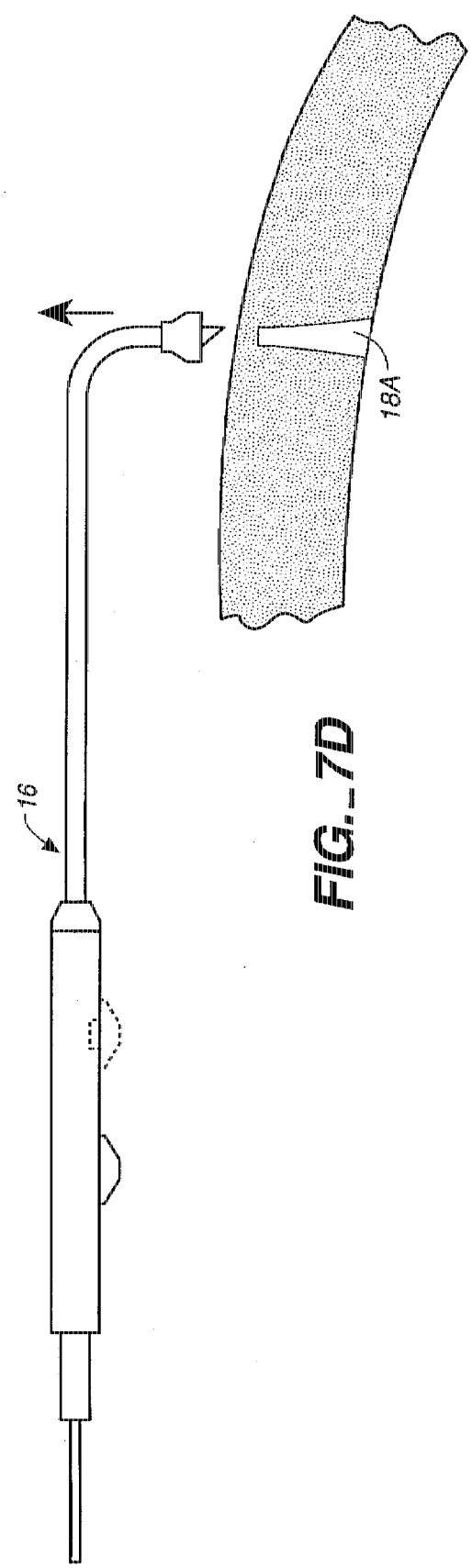

COMBINED MECHANICAL/OPTICAL SYSTEM FOR TRANSMYOCARDIAL REVASCULARIZATION

SPECIFICATION

1. Field of Invention

This invention relates to the field of laser surgery, and more particularly to improved laser surgery procedures and apparatus for increasing the flow of blood to heart muscle.

2. Background of the Invention

Medical science has developed a wide variety of methods for counteracting the effects of cardiovascular disease including open heart and by-pass surgery. Non-surgical procedures such as percutaneous transliminal coronary angioplasty, laser angioplasty, and atherectomy have also been developed.

One alternative to the aforementioned procedures is known as Laser Myocardial Revascularization (LMR). In LMR, channels are formed in the ventricle wall with a laser. These channels provide blood flow to ischemic heart muscle. A history and description of this method has been documented by Dr. M. Mirhoseini and M. Cayton on "Lasers in Cardiothoracic Surgery" in Lasers in General Surgery (Williams & Wilkins; 1989) pp. 216–233.

As described therein, a CO2 laser was used to produce channels in the ventricle from the epicardium through the myocardium. This procedure followed a surgical incision in the chest wall to expose the heart. Laser energy was transmitted from the laser to the epicardium by means of an articulated arm device of the type commonly used for CO2 laser surgery. The beam was coherent and traveled as a collimated beam of laser energy through the epicardium, the myocardium and the endocardium into the left ventricle cavity. The epicardium received the highest energy density and therefore normally had the largest area of heart tissue removed compared with the endocardium which was approximately 1 cm deep to the epicardium. The resultant channel through the myocardium was funnel-like. A problem associated with the above procedure arose because laser perforation of the epicardium caused bleeding from it outwardly from the left ventricle after the procedure. External pressure by the surgeon's hand on the epicardium of the heart was often needed to stop bleeding from the ventricle to the outside through the hole produced by the laser in the epicardium. However, this procedure was usually only partially successful because it resulted in a significant amount of blood loss and/or an excessive amount of time required to stop the bleeding. Both factors could jeopardize the success of the revascularization procedure.

In a proposed improvement in an LMR procedure described in Hardy U.S. Pat. No. 4,658,817, a needle was added to the distal tip of an articulated arm system, with a beam of laser energy being passed through the lumen of the needle. The metal tip of the needle of the device was used to pierce most of the myocardium and the laser beam then was used to create the desired channel through the remaining portion of the myocardium and through the adjacent endocardium. In the Hardy procedure, the hollow needle used to deliver laser light was subject to being clogged by tissue or blood which could flow into the needle, thus blocking the laser light from impinging the myocardium. Also, the metal rim of the needle could be damaged by the intense laser light and leave contaminating metal remains within the myocardium which are potentially hazardous.

Another proposed LMR procedure is described in the Aita, et al U.S. Pat. No. 5,380,316. Aita, commenting on the Hardy needle device, contends that mechanical piercing was undesirable because it entailed some degree of tearing of the pierced tissue, and that tearing often leads to fibrosis as the mechanical tear heals, a factor that severely diminishes the effectiveness of the LMR treatment. Aita, et al also contends that exposure to metal may cause fibrosis where the needle passes through tissue. The Aita, et al patent describes an elongated flexible lasing apparatus which is guided to an area exterior to the patient's heart and irradiates the exterior surface to form a channel through the epicardium, myocardium and endocardium. Thus, in the Aita et al procedure, the epicardium is irradiated at a high energy density and therefore should have a large area of heart tissue removed. Consequently, the Aita, et al procedure has the same problems and disadvantages as the prior Mirhoseini LMR procedure with respect to the aforementioned bleeding problem in the outer surface of the epicardium.

It is therefore a general object of the present invention to provide an improved method and apparatus for performing laser myocardial revascularization that solves the problems of the aforementioned prior devices and procedures.

A further object of the present invention is to provide a less invasive and safer method and apparatus for performing laser myocardial revascularization which does not diminish the effectiveness of the LMR treatment and eliminates the problem of excessive bleeding from the patient's epicardium following the channel forming procedure.

It is a further object of the present invention to provide a method and apparatus for performing laser myocardial revascularization which can access difficult to reach portions of the heart.

It is a further object of the present invention to provide a method and apparatus for performing laser myocardial revascularization which does require mechanical perforation or piercing of heart tissue to promote sealing of the epicardium but in such a way as to minimize the effect of any fibrosis which such perforation may cause, thereby maintaining the effectiveness of the LMR procedure.

It is a further object of the present invention to provide a method and apparatus for performing a TMR procedure that does not require that metal be passed through the newly created laser channel.

It is a further object of the present invention to have a cone-shaped channel formed whose wider end is at the endocardium and whose narrow end is closed beneath the epicardium to promote blood perfusion from the left ventricular cavity to avoid epicardial bleeding.

SUMMARY OF THE INVENTION

The present invention comprises a method and apparatus for combined mechanical/laser myocardial revascularization of a human heart that fulfills the aforesaid objectives. A mechanical piercing device combined with an elongated flexible lasing apparatus including an optical fiber bundle is inserted into the chest cavity of a patient. The apparatus is guided to an area exterior to a ventricle of the patient's heart. A hollow, tapered distal end of the device provides a piercing means that mechanically penetrates, micro-tears or spreads the epicardium muscle fibers of the heart. Within this hollow piercing means is the distal end of the optical fiber bundle which is now internal to the epicardium of the exterior wall of the heart. The laser energy is then dispersed from the distal end of the optical fiber bundle as it is advanced by the surgeon beyond the piercing means using a control knob on the handle of the operating device. Thus, the myocardium and not the epicardium is irradiated with laser energy. This enables the laser energy from said optical fiber distal end to form a channel as it moves into the left ventricular chamber without doing any laser irradiation of the epicardium which could cause operative bleeding, and thereby allowing the sealing of the epicardium after piercing means of the apparatus is removed. Any fibrosis caused by the mechanical piercing would promote healing of the epicardial surface. The laser energy is disbursed through the myocardium as a noncollimated, expanding beam so as to create a wider channel at the exit of the channel into the left ventricular cavity than within the myocardium.

Other objects, advantages and features of the present invention will be apparent to those skilled in the art from the following detailed description and the accompanying drawings.

DETAILED DESCRIPTION OF DRAWING

FIG. 1 is a schematic view in section of a human heart showing revascularization of the myocardium according to principles of the invention.

FIG. 2 is a view in side elevation showing a device embodying principles of the invention for implementing the revascularization procedure of FIG. 1.

FIG. 3 is an enlarged fragmentary view in section of the device shown in FIG. 2 showing details of the handle portion and the advancing mechanism for linear movement of the movable fiber element.

FIG. 3A is a reduced view in section taken along line 3A—3A of FIG. 3.

FIG. 3B is a reduced view in section taken along line 3B—3B of FIG. 3.

FIG. 4 is an enlarged fragmentary view of the forward head end of the device shown in FIG. 2 with the distal end of the movable fiber element shown extended in dotted lines.

FIG. 4A is a bottom end view of the device taken at line 4A—4A of FIG. 4.

FIG. 4B is a view in section of the forward end of the revascularization device.

FIG. 4C is a view in section of the forward end of the revascularization device taken along line 4C—4C of FIG. 4.

FIG. 5 is an enlarged fragmentary view of the distal end of the optical fiber bundle used with the device of FIG. 2.

FIG. 5A is an enlarged end view of the fiber bundle taken along line 5A—5A of FIG. 5.

FIGS. 6A–6D are enlarged views in section showing a revascularization device in operation during a typical revascularization procedure according to the principles of the invention.

FIGS. 7A–7D are enlarged views in section showing a revascularization device in operation during a modified revascularization procedure according to the principles of the invention.

DETAILED DESCRIPTION OF EMBODIMENT

With reference to the drawing, FIG. 1 diagrammatically depicts a human heart 10 with the epicardium 12 of the left ventricle 14 exposed where a Trans-Myocardial Revascularization (TMR) procedure according to the invention is to be performed. Preliminary to the procedure the surgeon makes an incision in the patient's chest to expose the outer wall (epicardium) of the heart's left ventricle. In a human heart the wall of the left ventricle, is comprised of an outer layer, the epicardium, the main muscle thickness, the myocardium, and the inner layer or endocardium. The epicardium is comprised of a smooth, moist serous membrane which is somewhat tougher than the other tissue layers of the heart muscle.

In accordance with the method of the present invention, the surgeon utilizes a hand-held device 16 which is manipulated and operated to form a series of revascularization channels 18 in the myocardium of the patient's heart at selected spaced apart locations. As will be described in greater detail below the device 16 has an enlarged head end member 20 with an annular end face 22 which is pressed against the outer surface of the epicardium by the surgeon. Extending beyond the end face is a hollow barb-like piercing member 24 which penetrates the epicardium to form an opening therein. Within the hollow piercing member is the distal end of an optical fiber bundle 26 which extends through and can be moved axially within the device 16. The proximal end of the optical fiber bundle 26 is connected to a source or generator 30 of laser energy which is preferably a Holmium laser that operates at a wave length in the range of 1.8–2.2 microns and a pulse frequency in the range of 2–25 Hertz. This type of laser is preferable because it provides high absorption efficiency, hemostosis and a moderate absorption range in myocardium tissue, and is compatible with optical fiber delivery.

At the laser generator, laser energy is supplied to the optical fiber bundle 26 which, at its distal end, as shown in FIGS. 5 and 5A, has a diameter of around 1.5 mm. The optical fiber bundle is comprised of a plurality (e.g. 37) of glass fibers 32 each having a diameter of 100 microns. These glass fibers are held together by a suitable plastic material 34, such a 353 ND Epoxy. Near its distal tip, the bundle preferable is surrounded by an annular tantalum marker 36 which serves to retain the bundle closely packed in a proper, geometric boundary. Overlapping the marker 36 and surrounding the bundled fibers 32 is a plastic protective sheath 38 such as polypropelene having a wall thickness of 0.004 inches.

As shown in greater detail in FIG. 2, the device 16 comprises a handle 40, a flexible neck member 42 to which the distal end head member 20 is attached and through which the optical bundle 26 extends.

In the embodiment shown, the neck member 42 of the device 16 is a tubular member having a uniform outside diameter (e.g. 0.120 inches) and inside diameter (e.g. 0.094 inches) preferably bent into an angular "J" shape within which the optical fiber bundle 26 is slidable. This neck portion is preferably made from a stainless steel which is heat treated to make it malleable and thus somewhat flexible. This enables the neck portion to be easily bent so that its distal end head member 20 can be positioned to accommodate the specific requirements of the surgical procedure being performed.

The flexible neck member 42 is fixed to the handle 40 which is a rigid tubular member having a cylindrical lumen 44 through which extends the optical fiber bundle 26 whose proximal end is connected to the laser energy source 30.

Slidably situated within the cylindrical lumen 44 as shown in FIG. 3, is a movable shuttle 46 of stainless steel which surrounds and to which is firmly fixed the fiber bundle 26 by means of a friction fit therewith. A silastic tube 47 is contained within a chamber located at the proximal end of the movable shuttle 46. A threaded tensioning nut 49 threads into the proximal end of the movable shuttle 46 which compresses the silastic tube 47 causing the inside wall of the tube to compress around the fiber bundle 26 to produce the friction fit.

On the upper side of the handle portion is an enlarged slot 48 (See FIGS. 3A and 34) within which is located a thumb operated control knob or block 50 for moving the fiber bundle 26 axially through the device 16 and beyond its distal head end member 20. This thumb engaging control knob 50 preferably having a non-slip serrated upper surface, is movable axially within the slot 48 and is attached to the shuttle 46 near one end thereof by a short screw 52. Thus, as readily seen, with one hand the operating surgeon can move the fiber bundle 26 within the handle 40 and thus move the distal tip of the bundle beyond the barb 24 by light thumb pressure on the control knob 50.

Fixed to the distal end of the tubular neck portion and shown in greater detail in FIGS. 4, and 4A–4C is the enlarged positioning and stabilizing head member 20 for the device 16. As shown, this head member 20 has an annular flange portion with its generally planar end surface 22 that is transverse and preferably perpendicular to the axis of the inner passage and the fiber bundle 26 therein. One or more circular grooves 4 are provided in the end surface 22 so that the head member will retain its position when pressed firmly against the epicardium of the heart. Extending from the end surface 22 of the head member for a short distance (typically around 0.2 inches) is a beveled distal end portion of the curved tubular neck member 42 which forms the piercing member 24. Thus, as shown in FIG. 4 this piercing member is generally tubular and has an annular end surface 56 in a plane that cuts through the center line of the neck member at an angle of around 60°.

As shown in FIG. 3, the tubular neck member 42 has an enlarged plug member 58 with a series of external threads 60 at its proximal end which are threadedly attached to an internally threaded head end portion 62 of the handle 40. It is desirable that the "J" shaped neck member 42 be rotatably adjustable in its operating position relative to the advancing knob 50 on the handle. This is in order to accommodate the different grasping modes preferred by different surgeons. In order to provide this adjustability, a threaded spacer nut 64 is placed within the threaded head end portion 62 of the handle, which can be moved to a desired axial position therein. Thus, when the threaded end of the neck member 42 is threaded in the handle and bottomed against the spacer nut 64, the distal or head end member 20 of the neck member will be oriented in a fixed position relative to the control knob 50 on the handle. If it is desired to change the head end orientation, this can be done by moving the spacer nut 64 in or out within the handle's threaded end portion.

The inner end of both the spacer nut 64 and the plug member 58 have a tapered recess 65 that provides a wider opening to facilitate the ease of threading the fiber bundle 26 through the handle. From the foregoing, it is seen that the construction arrangement of parts provides a device that is easy to assemble, clean and adjust, when necessary.

The use of the device 16 in a Transmyocardial Revascularization (TMR) procedure according to the invention is illustrated in FIG. 1 and sequential FIGS. 6A–6D. After the surgeon makes an opening in the patient's chest to expose the left ventricle outer wall of the heart, the device 16, connected to its laser source is held by the surgeon.

During the TMR procedure the device 16 is maneuvered as shown in FIG. 6A so that its head end 20 is placed against the epicardium of the left ventricle. The annular end face 22 of the head end member 20 serves as a stop as it is pressed against the outer surface of patient's heart. As this is done, as shown in FIG. 6A, the piercing member 24 penetrates the tougher outer epicardium layer of the heart muscle while the distal end of the fiber bundle 26 is just inside the piercing member. With the head end member and the piercing member in place, the fiber bundle is moved forward from the distal end of the device by movement of the control knob 50 as laser pulses are simultaneously transmitted from its distal end, as shown in FIG. 6B. As laser energy is emitted, the distal end of the optical fiber bundle proceeds through the myocardium portion of the ventricle wall and ultimately through the inner endocardium layer (FIG. 6C). As the fiber bundle advances and pulses laser energy it forms an expanding channel 18 in the myocardium that provides the revascularization of the heart muscle.

An important feature relative to the present invention is that the epicardium is pierced or penetrated mechanically but is not subjected to laser energy. The piercing member 24 penetrates through the epicardium with only a minimal damage to tissue and while protecting the distal end of the fiber bundle 26. Thus, after the channel 18 is fully formed, the fiber bundle 26 is retracted by the control knob 50 and the piercing member 24 is removed, as shown in 6D. The opening caused by the piercing member normally closes due to the resiliency of the muscle fibers in the epicardium so that there is no bleeding or only minimal bleeding on the outer surface of the heart.

An alternative, somewhat modified method according to the invention is illustrated in FIGS. 7A–7D. Here, the device 16 is placed, as in the previous method, with its head end 20 against the epicardium so that the piercing member 24 provides a small initial opening through it. At this point, the surgeon advances the fiber bundle 26 using the control knob 50 on the device to force the fiber bundle through the myocardium and the endocardium without yet actuating the laser source. (FIG. 7B) Now, as shown in FIG. 7C, as the fiber bundle 26 is being slowly retracted by the surgeon, the laser source is activated. Thus, as the fiber bundle is retracted, a conical channel 18A is formed in the myocardium, as in the previous method. As the distal end of the fiber bundle nears the head end member 20, against the epicardium. The laser power is deactivated, so that again, no laser hole is made through the epicardium. When the device 16 is removed from epicardium, again no bleeding from the newly formed channel occurs, and the surgeon can continue the TMR procedure by moving the device to another location on the outer surface of the left ventricle of the patients heart.

To those skilled in the art to which this invention relates, many changes in construction and widely differing embodiments and applications of the invention will make themselves known without departing from the spirit and scope of the invention. The disclosure and the description herein are purely illustrative and are not intended to be in any sense limiting.

What is claimed is:

1. A surgical device for performing a transmyocardial revascularization (TMR) surgical procedure on a patient's heart, the device comprising:

a handle portion;

a tubular neck portion on the handle portion;

an enlarged head portion on a distal end of the neck portion, the head portion is a radial flange member forming a distal end contact surface for stabilizing the device when engaging the heart;

an optical fiber means for transmission of laser energy to a terminus of the fiber means thereby effectuating tissue ablation, the fiber means i) has a proximal end adapted for connection to a laser source and ii) is extendible through the handle, the neck portion and the enlarged head portion; and fiber optic adjustment means disposed on the handle portion for moving the optical fiber means within the handle portion and the neck portion, whereby the fiber means can move forward from the enlarged head portion as laser energy is emitted from the fiber means during the TMR surgical procedure.

2. The surgical device as described in claim 1 wherein the handle portion has an axial lumen, a movable shuttle within the axial lumen is connected to the optical fiber means, the optical fiber means extends axially within the lumen; and a control knob fixed to the shuttle and extending outwardly from the handle portion; whereby the optical fiber means can be moved axially within the handle portion by movement of the control knob.

3. The surgical device as described in claim 1 wherein the tubular neck portion has an offset curved shape at the neck portion.

4. The surgical device as described in claim 1 wherein the tubular neck portion is made of a malleable material thereby allowing orientation changes of the enlarged head portion relative to the handle portion.

5. The surgical device as described in claim 1 wherein the handle portion has a threaded socket, the tubular neck portion having a threaded section that is attached to the threaded socket; and an adjustment nut in the threaded socket facilitates the fixed orientation of the head member relative to the handle portion.

6. The surgical device as described in claim 1 wherein the device further includes a tapered piercing means extending axially from the enlarged head portion.

7. The surgical device as described in claim 1 wherein the enlarged head portion has a circular end face having a diameter at least 0.375 inches.

8. The surgical device as described in claim 6 wherein the tapered piercing means is a tapered distal end portion of the neck portion which extends through the head member and beyond the end surface.

9. The surgical device as described in claim 8 wherein the tapered distal end portion extends approximately 0.20 inches beyond the end surface.

10. A surgical device for performing a transmyocardial revascularization (TMR) surgical procedure on a patient's heart, the device comprising:

a handle portion;

a tubular neck portion on the handle portion;

an enlarged head portion connected to a distal end of the neck portion, the head portion is a radial flange member forming a distal end contact surface for stabilizing the device when engaging the heart;

a tapered piercing means for tissue piercing which extends axially from the enlarged head portion and beyond the distal contact surface, thereby stabilizing the device during the TMR surgical procedure;

an optical fiber means for transmission of laser energy to a terminus of the fiber means for ablating tissue, the fiber means i) has a proximal end adapted for connection to a laser source and ii) is extendible through the handle, the neck portion and the enlarged head portion; and fiber optic adjustment means disposed on the handle portion for moving the optical fiber means within the handle portion and the neck portion, whereby the fiber means can move forward from the enlarged head portion as laser energy is emitted from the fiber means during the TMR surgical procedure.

11. The surgical device as described in claim 10 wherein the handle portion has an axial lumen, a movable shuffle within the axial lumen is connected to the optical fiber means, the optical fiber means extends axially within the lumen; and a control knob fixed to the shuffle and extending outwardly from the handle portion; whereby the optical fiber means can be moved axially within the handle portion by movement of the control knob.

12. The surgical device as described in claim 10 wherein the tubular neck portion has an offset curved shape at the neck portion.

13. The surgical device as described in claim 10 wherein the tubular neck portion is made of a malleable material thereby allowing orientation changes of the enlarged head portion relative to the handle portion while maintaining a fixed position when used in the TMR surgical procedure.

14. The surgical device as described in claim 10 wherein the handle portion has a threaded socket, the tubular neck portion having a threaded section that is attached to the threaded socket; and an adjustment nut in the threaded socket to facilitate the fixed orientation of the head member relative to the handle portion.

15. The surgical device as described in claim 10 wherein the tapered distal end portion extends approximately 0.20 inches beyond the end surface.

16. The surgical device as described in claim 10 wherein the enlarged head portion has a circular end face having a diameter of at least 0.375 inches.

* * * * *

UNITED STATES PATENT AND TRADEMARK OFFICE
CERTIFICATE OF CORRECTION

PATENT NO. : 5,713,894
DATED : February 3, 1998
INVENTOR(S) : Douglas Murphy-Chutorian and Stuart D. Harman It is certified that error appears in the above-identified patent and that said Letters Patent is hereby corrected as shown below:

On the title page item [56],
in the "Attorney, Agent or Firm" section, insert before
"Janet Kaiser Castaneda," --"Roger W. Erickson"-- and after
"Janet Kaiser Castaneda," insert --"Christopher N. Sears"--.

Signed and Sealed this

Twenty-eighth Day of April, 1998

Attest:

BRUCE LEHMAN

Attesting Officer

Commissioner of Patents and Trademarks